(12) United States Patent
Dunham et al.

(10) Patent No.: US 7,192,031 B2
(45) Date of Patent: Mar. 20, 2007

(54) EMITTER ARRAY CONFIGURATIONS FOR A STATIONARY CT SYSTEM

(75) Inventors: Bruce M. Dunham, Mequon, WI (US); Colin R. Wilson, Niskayuna, NY (US); John Scott Price, Wauwatosa, WI (US)

(73) Assignee: General Electric Company, Schnectady, NY (US)

( * ) Notice: Subject to any disclaimer, the term of this patent is extended or adjusted under 35 U.S.C. 154(b) by 170 days.

(21) Appl. No.: 10/708,048

(22) Filed: Feb. 5, 2004

(65) Prior Publication Data

US 2005/0175151 A1    Aug. 11, 2005

(51) Int. Cl.
*H01J 35/00* (2006.01)
*H01J 35/06* (2006.01)
(52) U.S. Cl. ..................... 278/122; 378/136
(58) Field of Classification Search ............ 378/119, 378/122, 124, 134, 136, 137; 313/495, 351, 313/309
See application file for complete search history.

(56) References Cited

U.S. PATENT DOCUMENTS

| | | | |
|---|---|---|---|
| 5,317,307 A * | 5/1994 | Thomas, Jr. ............ 340/815.45 |
| 6,333,968 B1 * | 12/2001 | Whitlock et al. ............ 378/136 |
| 6,385,292 B1 | 5/2002 | Dunham et al. |
| 6,674,837 B1 * | 1/2004 | Taskar et al. ............... 378/122 |
| 6,980,627 B2 * | 12/2005 | Qiu et al. .................... 378/122 |

* cited by examiner

*Primary Examiner*—Edward J. Glick
*Assistant Examiner*—Irakli Kiknadze
(74) *Attorney, Agent, or Firm*—Peter Vogel

(57) ABSTRACT

An field emitter array system (10) includes a housing (50). An emitter array (80) generates an electron beam and has multiple emitter elements (81) that are disposed within the housing (50). Each of the emitter elements has multiple activation connections (92).

27 Claims, 6 Drawing Sheets

EMITTER ARRAY CONFIGURATIONS FOR A STATIONARY CT SYSTEM

BACKGROUND OF INVENTION

The present invention relates generally to field emitter arrays and field emitter array systems, such as computed tomography (CT) imaging systems. More particularly, the present invention relates to emitter array configurations for field emitter array systems.

A CT imaging system typically includes a gantry that rotates at various speeds to create 2D and 3D images. The gantry contains an x-ray source, such as an x-ray tube that generates x-rays across a vacuum gap between a cathode and an anode. The x-ray source projects a fan-shaped beam that is collimated to lie within an X-Y plane of a Cartesian coordinate system, which is generally referred to as the "imaging plane". The x-ray beam passes through the object being imaged, such as a patient. The beam, after being attenuated by the object, impinges upon an array of radiation detectors. Each detector element of the array produces a separate electrical signal that is a measurement of the beam attenuation at the detector location. The attenuation measurements from all the detectors are acquired separately to produce a transmission profile.

A desire exists to utilize an x-ray system without a rotating gantry, due to complexity and costs involved therein. One system that does not require a rotating x-ray source includes the use of a large vacuum chamber, which incorporates an electron gun and ring-shaped targets to produce x-rays. An electron beam emerges from the gun, several feet away from the patient, travels a bent path toward and impinges on the target material to produce x-rays. The single fairly high power electron beam sweeps out a circle or ring that surrounds the patient, to produce a "scan" effect. Such a system requires a large vacuum system to enclose the electron beam trajectory and a complicated beam deflection system, to accurately steer the beam.

Another system that does not require a rotating gantry is commonly referred to as a stationary CT (SCT) system. The SCT system provides an x-ray source that reduces the complexity of the scanning system and does not require a rotating x-ray source. However, although the complexity of high voltage high power x-ray tubes is generally due to the vacuum enclosure and the careful preparation of the surfaces and volumes of material that are enclosed therein, the complexity of an SCT system can also be due to the number of activation lines and connections associated with the large number of emitter elements of an emitter array.

An SCT system can utilize hundreds to thousands of electron emitters in the generation of x-rays. Each of the emitter elements is addressed in turn via an associated bias or activation line and at appropriate time intervals. Due to the large number of emitter elements, there can exist an equally large quantity of associated activation lines and connections. The large number of activation lines need to pass through the vacuum chamber of the x-ray source to supply the emitter elements, thus there necessitates a large number of vacuum joints.

There is an unavoidable leak rate associated with any feedthrough device. This leak rate is compensated for through the use of pumps, both active and passive, so that the gas pressures do not rise to values inimical to electron source performance.

Due to the complexity and poor reliability of utilizing such a large number of vacuum joints and the desire to decrease the complexity of an SCT system, there exists a need for an improved system and method of controlling the emitter elements.

SUMMARY OF INVENTION

The present invention provides a field emitter array system that includes a housing. An emitter array generates an electron beam and has multiple emitter elements that are disposed within the housing. Each of the emitter elements has multiple activation connections.

The embodiments of the present invention provide several advantages. One such advantage is the provision of an x-ray source having an emitter array where each emitter element therein has multiple activation connections. In so doing, the stated embodiment minimizes the number of activation control lines for the emitter array and thus, the number of feedthroughs from atmosphere into the vacuum of the x-ray source. The reduction in the number of activation lines and feedthroughs reduces the complexity and manufacturing costs of the x-ray source.

Another advantage provided by an embodiment of the present invention, is the provision of mapping two-dimensional and three-dimensional activation schemes to one-dimensional physical configurations. This allows for the generation of arc-shaped emitter arrays having minimal activation control lines.

Yet another advantage provided by an embodiment of the present invention, is the provision of an x-ray source having multiple emitter array blocks, each of which having associated address lines. This further minimizes the number of feedthroughs of an x-ray source.

The present invention itself, together with attendant advantages, will be best understood by reference to the following detailed description, taken in conjunction with the accompanying figures.

BRIEF DESCRIPTION OF DRAWINGS

For a more complete understanding of this invention reference should now be had to the embodiments illustrated in greater detail in the accompanying figures and described below by way of examples of the invention wherein.

DETAILED DESCRIPTION

Figure 1:
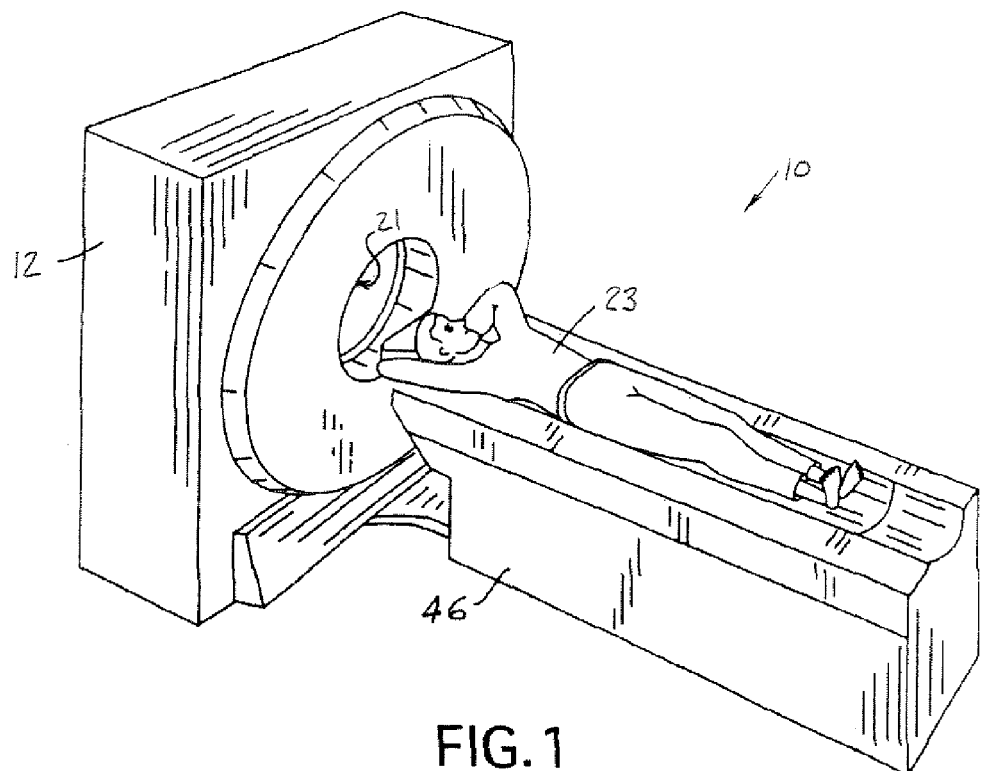
FIG. 1 is a perspective view of a stationary CT imaging system in accordance with an embodiment of the present invention.

In the following figures the same reference numerals will be used to refer to the same components. While the present invention is described with respect to x-ray source emitter array configurations utilized within a stationary computed tomography (SCT) system, the present invention may be adapted and applied to various systems including CT systems having a rotating gantry and other x-ray systems that utilize emitter arrays. The present invention may also be applied to flat panel displays and other systems, which include field emitter arrays.

In the following description, various operating parameters and components are described for one constructed embodiment. These specific parameters and components are included as examples and are not meant to be limiting.

Although the embodiments of FIGS. 1–4 are described below with respect to a stationary gantry, the present invention may be applied to a rotating gantry. For example, a gantry may be rotated at a slow rate while utilizing x-ray sources with sequentially activated emitter elements.

Figure 2:
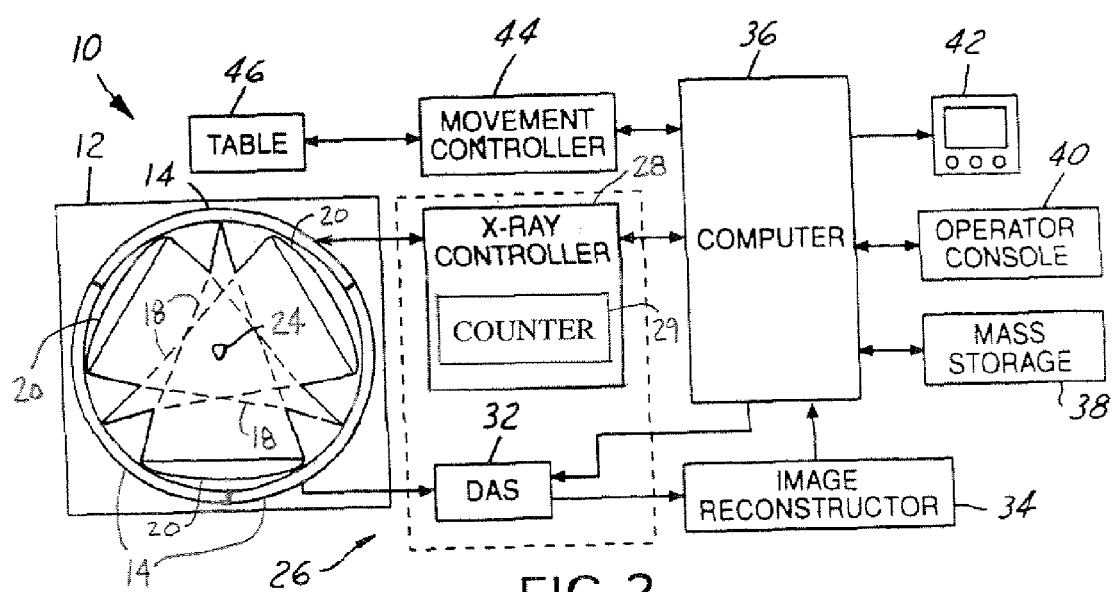
FIG. 2 is a block diagrammatic view of the stationary CT imaging system in accordance with an embodiment of the present invention.

Referring now to FIGS. 1 and 2, a perspective view and a block diagrammatic view of a field emitter array system or more particularly an SCT imaging system 10 in accordance with an embodiment of the present invention is shown. The SCT system 10 includes a gantry 12 that has multiple x-ray sources 14, which project beams of x-rays 18 toward detector arrays 20, within a patient volume 21. Each detector array 20 includes an array of detection elements (not shown), which generate electrical signals in response to the intensity of the impinging x-ray beams 18 and hence, the attenuation of the beams 18 as they pass through the patient 23 or object 24. The x-ray sources 14 may be longitudinally offset from the detector arrays 20 or activated such that there is no interference therebetween. Although three x-ray sources are shown, each of which having a semi-circular or arc shape, any number of x-ray sources may be used. The x-ray sources may have various sizes and shapes.

The operation of the x-ray sources 14 is governed by a control mechanism 26 of the SCT system 10. The control mechanism 26 includes an x-ray controller 28 that provides power and timing signals to the x-ray sources 14. The x-ray controller 28 includes a counter 29. The counter 29 may be used as an incrementing device or may be in the form of a random number generator. The counter 29 is further described with respect to the embodiment of FIG. 8. A data acquisition system (DAS) 32, in the control mechanism 26, samples the analog data from the detector arrays 20 and converts the data to digital signals for subsequent processing. An image reconstructor 34 receives the sampled and digitized x-ray data from the DAS 32 and performs high-speed image reconstruction. The reconstructed image is applied as an input to a computer 36, which stores the image in a mass storage device 38.

The computer 36 also receives and supplies signals via a user interface or graphical user interface (GUI). Specifically, the computer 36 receives commands and scanning parameters from an operator console 40. A video display 42 allows the operator to observe the reconstructed image and other data from the computer 36. The operator supplied commands and parameters are used by the computer 36 to provide control signals and information to the x-ray controller 28, the DAS 32, and the table movement controller 44. The table movement controller 44 controls the operation of the table 46.

Figure 3:
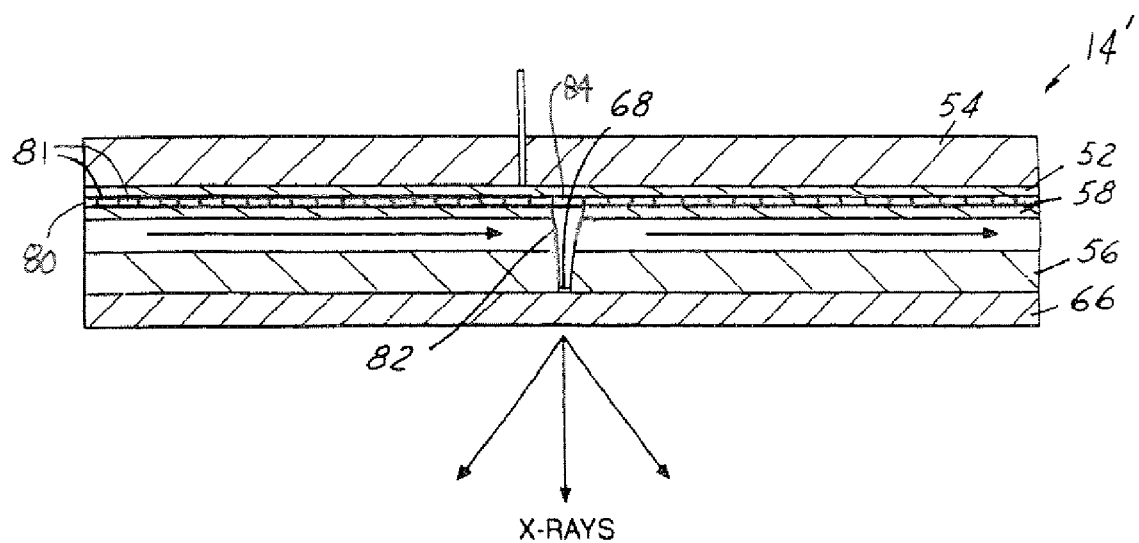
FIG. 3 is a front longitudinal cross-sectional view of a solid state x-ray tube in accordance with an embodiment of the present invention.
Figure 4:
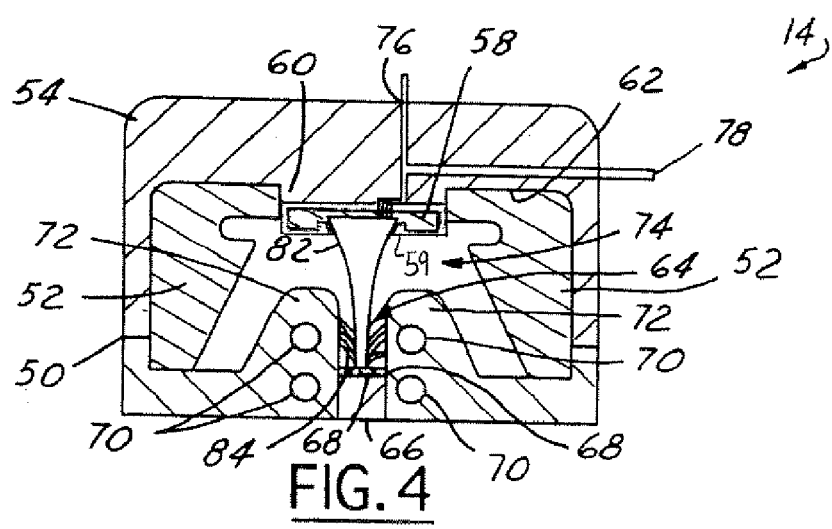
FIG. 4 is a cross-sectional side view of a solid-state x-ray tube in accordance with an embodiment of the present invention.

Referring now to FIGS. 3 and 4, a front longitudinal cross-sectional view and a cross-sectional side view of a solid-state x-ray source or x-ray tube 14' in accordance with an embodiment of the present invention is shown. The x-ray tube 14' has a housing 50 that is sealed to provide a vacuum therein. Housing 50 has a support frame 52 that may be formed of an insulative material, such as alumina.

Housing 50 has a support portion 54 and a cooling block portion 56. Support portion 54 may be formed of various compounds, such as a high voltage epoxy compound. The cooling block portion 56 is thermally and electrically conductive. Cooling block portion 56 may be formed of a conductive material, such as copper.

Support portion 54 is generally an elongated semi-tubular shape. As illustrated, support portion 54 is u-shaped. Support portion 54 is used to position one or more cathodes 58 (only one is shown), within one or more emitter array blocks 59 (only one is shown), for generating electrons. The cathode 58 is coupled within the array block 59 and is supported by a cathode support portion 60, which is integrally molded with support portion 54. The cathode 58 and the array block 59 may be integrally formed as a single unit or may be separate units as shown. When more than one cathode and more than one array block are utilized, the array blocks may be coupled in series to form an arc around the patient volume 21.

Cooling block portion 56 has an elongated channel 64 or beam opening extending therethrough. Elongated channel 64 has an x-ray transmissive window 66 disposed therein. The x-ray transmissive window 66 is formed from a thermally and electrically conductive material, such as a carbon-based material like graphite. Other suitable materials known to those skilled in the art may be used, such as beryllium, or aluminum.

An anode 68 is formed directly and operatively adjacent to the x-ray transmissive window 66. The anode 68 may be formed of a thin metallic layer 68, such as one formed of foil. The thin film anode 68 may be formed of a high atomic weight material such as tungsten or uranium. The anode 68 may be formed as a thin film, which is deposited directly onto the window 66. The anode 68 is thermally coupled to the cooling block portion 56 for cooling thereof. The anode 68 may also be formed from a relatively thin layer of tungsten or tungsten alloy.

The cooling block portion 56 has multiple cooling tubes 70 extending therethrough. Cooling fluid or air may be circulated through the cooling tubes 70 to reduce the temperature of the cooling block portion 56 and ultimately the temperature of the anode 68.

The support portion 54 and the cooling block portion 56 define a vacuum chamber 74 therein. The vacuum chamber 74 extends substantially along the length of the support portion 54 and the cooling block portion 56.

The cathode 58 has a plurality of gating connections 76 coupled thereto. Gating connections 76 control the turning "ON" and "OFF" of the cathode 58. High voltage input 78 is coupled to the cathode 58 to provide the necessary potential for the generation of electrons. Both the gating connections 76 and the high voltage input 78 may be formed through the support portion 54.

Cathode 58 is preferably formed of an elongated emitter array 80 having multiple emitter elements 81. Various types of emitter elements may be used. For example, ferro-electric emitters may be used to create an electron emission in the form of a small relatively narrow width beam that impinges on the anode 68. Another type of cathode that may be used is a thin film emission cathode. Photo emitters may also be used for cathode 58. Photo emitters may, for example, be in the form of compact laser diode arrays. Emission occurs according to the order in which the laser beams of sufficient power and proper wavelength "address" the emitters by raster scanning of the emitters 81.

Emitter elements 81 may be selectively turned ON and OFF to form the electron beams 82 (only one is shown and is illustrated for element 84). The emitter elements 81 may be sequentially activated, to effectively allow the beams 82 to be sequentially generated across the cathode 58 in a scanned manner, or may be non-sequentially activated. The emitter elements 81 may be arbitrarily or randomly activated to improve image quality. The electrons are released from the emitter elements 81 and are directed toward the anode 68. When the electrons impinge upon the anode 68, x-rays are released through the window 66. Thermal energy absorbed into the cooling block 56 is removed through the cooling channels 70.

Figure 5A:
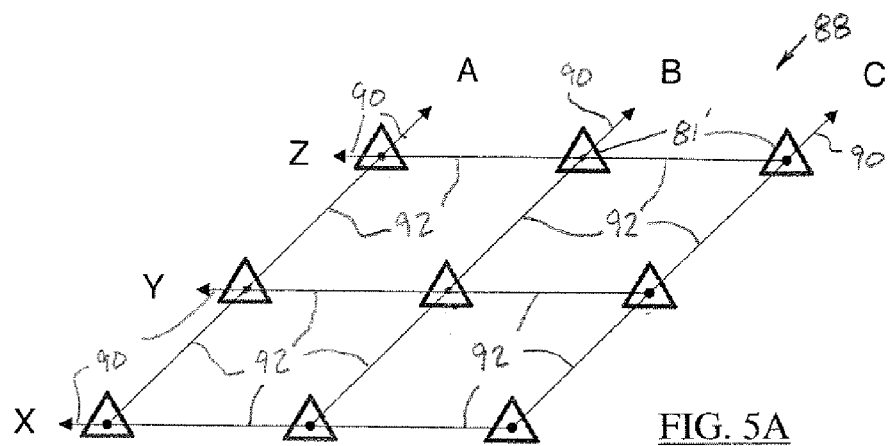
FIG. 5A is a two-dimensional diagram representation illustration of an activation scheme for multiple emitter elements in accordance with an embodiment of the present invention.

Referring now to FIG. 5A, a two-dimensional diagram representation of an activation scheme for multiple emitter elements 81' in accordance with an embodiment of the present invention is shown. For example purposes, a three-by-three array 88 is shown. The array 88 has three rows, designated by X, Y, and Z, and three columns, designated by A, B, and C. The elements 81' are activated or addressed by six activation control lines 90, which are shared among the elements 81'. Note that each element 81' has two associated activation connections 92. Each element 81' also has two associated activation lines 90, one from rows X–Z and one from columns A–C. Thus, for an emitter array in this configuration, with N rows and N columns or $N^2$ elements, there are 2N activation lines. As another example, a 900-emitter array in this configuration would utilize 60 activation lines. The activation lines 92 may be considered as 60 vacuum feedthrough lines.

Figure 5B:
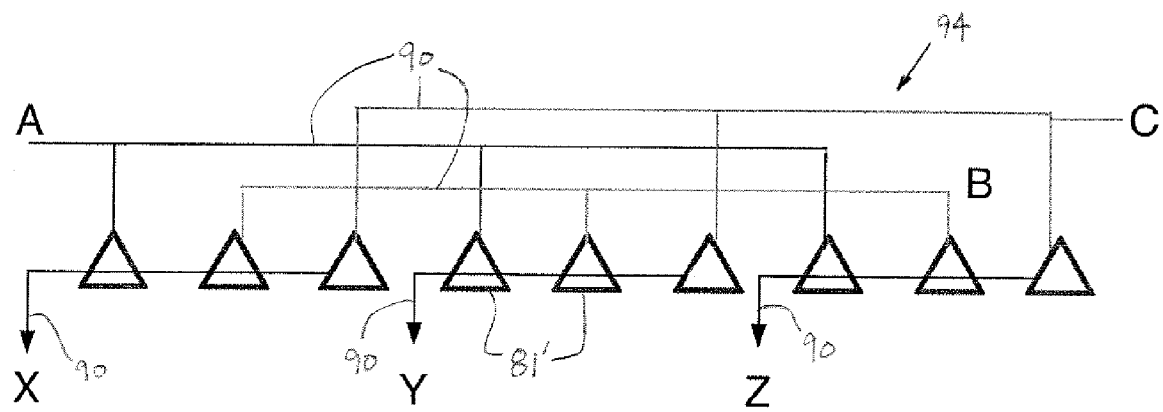
FIG. 5B is a one-dimensional diagram representation of a two-dimensional mapping of the emitter elements of FIG. 5A in accordance with an embodiment of the present invention.

Referring now to FIG. 5B, a one-dimensional diagram representation of a two-dimensional mapping of the emitter elements 81' in accordance with an embodiment of the present invention is shown. The two-dimensional array 88 can be mapped to a one-dimensional array 94, as shown. The elements 81' are arranged in a row for sequential linear activation thereof.

Figure 5C:
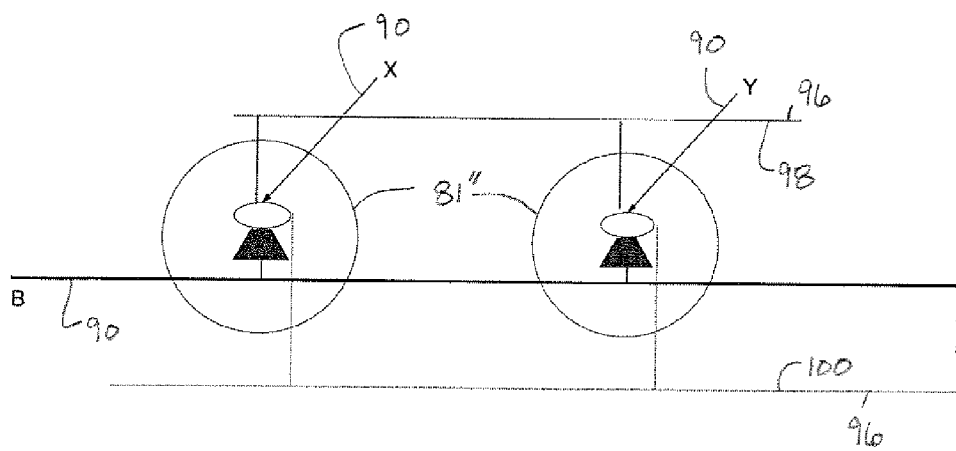
FIG. 5C is a schematic diagram of sample emitter elements in accordance with an embodiment of the present invention.

Referring now to FIG. 5C, a schematic diagram of sample emitter elements that may be used for the two-dimensional scheme of FIG. 5A is shown in accordance with an embodiment of the present invention. Two emitter elements 81" are shown as an example. The elements 81" have the activation lines 90. A pair of common focusing lines 96 are also shown and may be coupled to each element 81". The focusing lines 96 are used to control the width and length of the focal spot of each element 81". A first focusing line 98 is used to control focal spot length and a second focusing line 100 is used to control focal spot width.

Figure 6A:
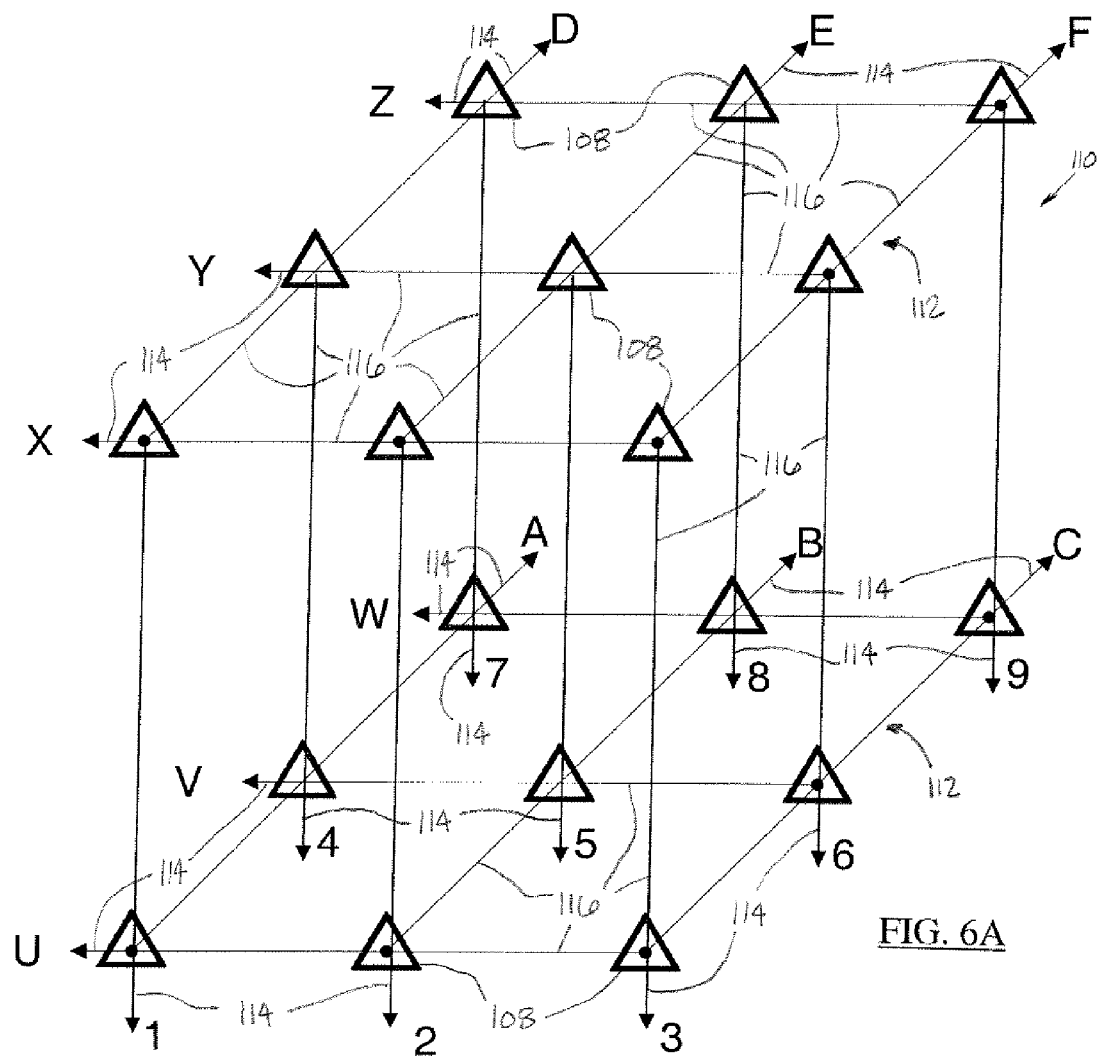
FIG. 6A is a three-dimensional diagram representation of an activation scheme for multiple emitter elements in accordance with another embodiment of the present invention.

Referring now to FIG. 6A, a three-dimensional diagram representation of an activation scheme for multiple emitter elements 108 in accordance with another embodiment of the present invention is shown. A three-dimensional emitter array 110 is shown. The three-dimensional array 110 includes a pair of two-dimensional arrays 112 each of which having three rows and three columns, designated by U–Z and A–F. The rows U–Z and the columns A–F are activated by 21 activation control lines 114, which are shared among the elements 108. Note that each element 108 has three associated activation connections 116. Each element 108 also has three associated activation lines 114, one from rows U–Z, one from columns A–F, and one from lines 1–9. Thus, for an emitter array in this configuration, with $N^3$ elements, there are 3N activation lines. As another example, an emitter array in this configuration having 1000 emitter elements would utilize 30 activation lines. A 3D-to-1D mapping may be generated for the array 110, similar to the mapping illustrated in FIG. 5B, whereby the elements 108 are arranged in a single row.

Figure 6B:
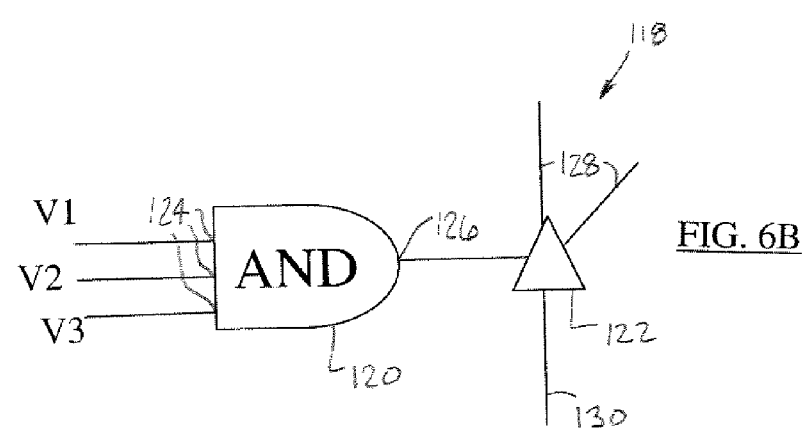
FIG. 6B is a schematic diagram of a sample emitter element circuit in accordance with another embodiment of the present invention.

Referring now to FIG. 6B, a schematic diagram of a sample emitter element circuit 118 that may be utilized in replacement of the emitter elements 81' and 108 is shown in accordance with another embodiment of the present invention. The emitter circuit 118 is shown with respect to the configuration of FIG. 6A. The emitter circuit 118 includes an AND gate 120 and an emitter 122. Although the AND gate 120 is shown as having three inputs 124, the AND gate 120 may have any number of inputs. When all three inputs 124 are "HIGH" the output 126 is HIGH and in turn activates the emitter 122. The emitter 122 may also have a pair of focusing control lines 128 and an address line 130. The address line 130 may be coupled as an input to the AND gate 120 or be coupled directly to the emitter 122, as shown. The address line 130 may be utilized when multiple emitter array element blocks are utilized, which is described in further detail below with respect to the embodiment of FIG. 7.

For the two-dimensional schemes of FIGS. 5A–C, the emitter elements 81' may be in the form of diodes and have two legs corresponding to the two connections 92. For the three-dimensional scheme of FIG. 6A the emitter elements 108 may be in the form of transistors, configured to form a 3-input AND gate or similar, and have three legs corresponding to the three connections 116. Of course, various other emitter elements known in the art may be utilized. The emitter elements 81' and 108 may be in the form of field emitters, carbon nanotube emitters, dispenser cathodes, or other emitters known in the art.

Figure 7:
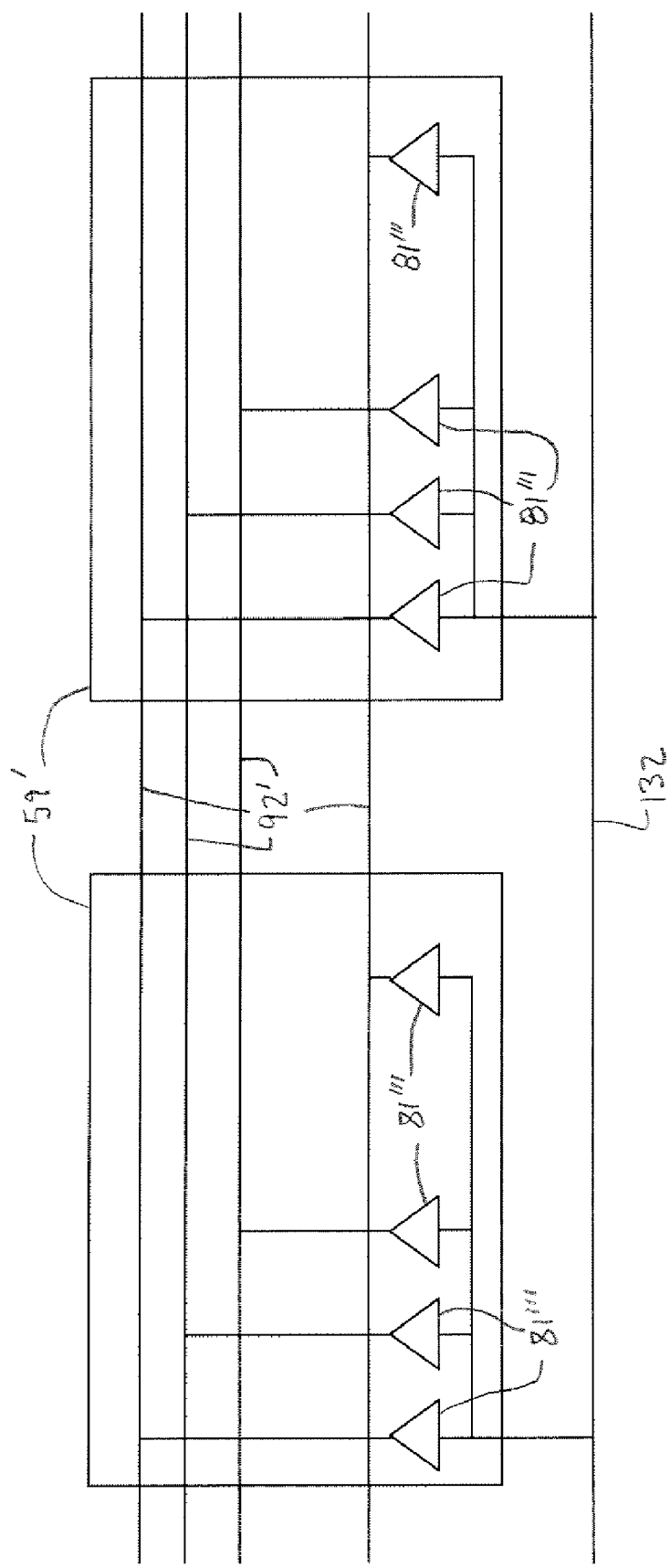
FIG. 7 is a schematic and block diagrammatic view illustrating a series of emitter array blocks for a two-dimensional scheme in accordance with another embodiment of the present invention.

Referring now to FIG. 7, a schematic and block diagrammatic view illustrating a series of emitter array blocks 59' for a two-dimensional scheme in accordance with another embodiment of the present invention is shown. Each emitter array block 59' includes a series of emitter elements 81'''. Each block 59' is activated by the address line 132. Each emitter element 81''' is activated via the connections 92' when the associated block is addressed. The connections 92' are shared between the blocks 59'. The emitter elements 81''' have the same number of activation or address lines as the emitter elements 81''' of FIG. 5A. A similar configuration may be formed for a three-dimensional scheme.

Figure 8:
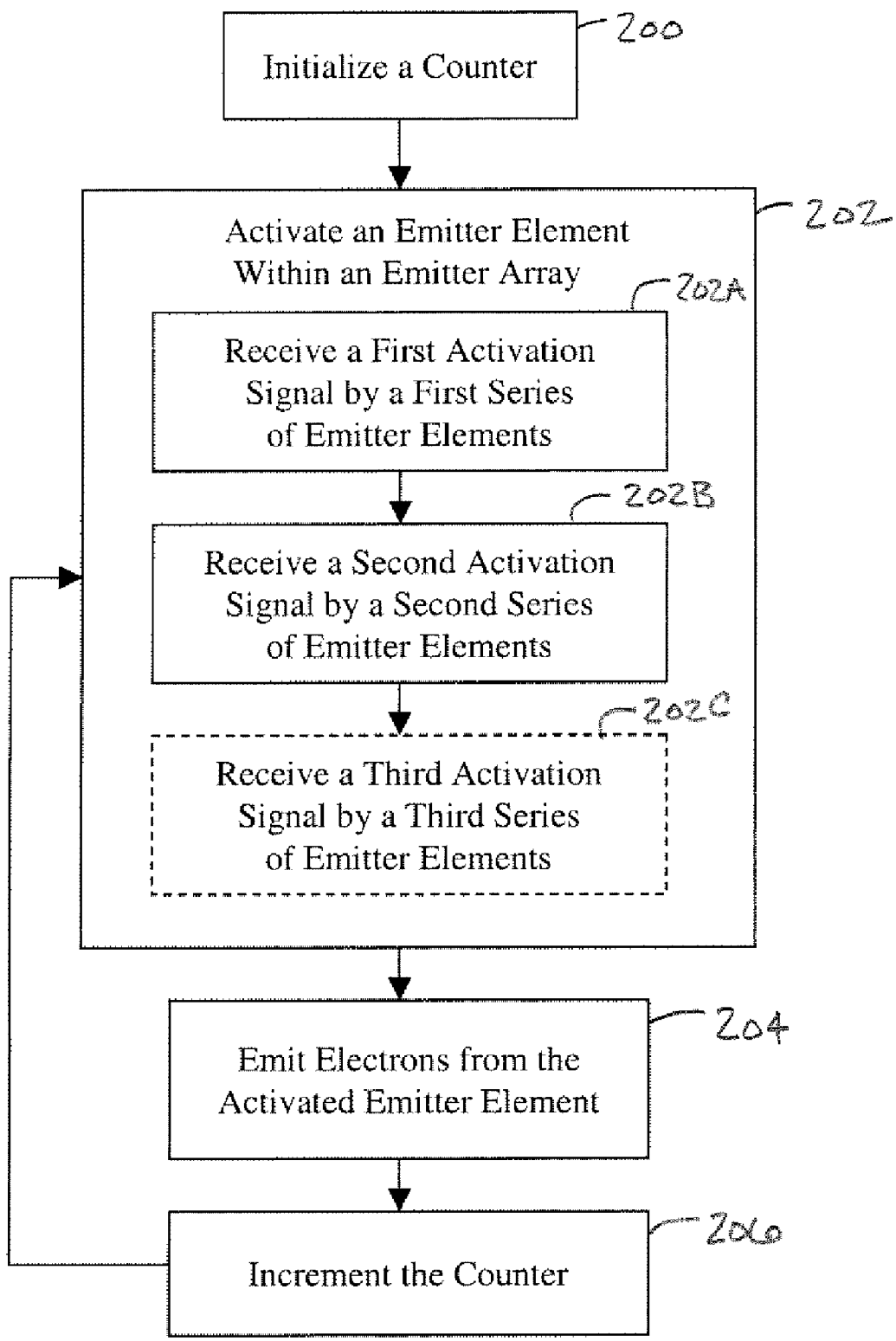
FIG. 8 is a method of activating emitter elements of an x-ray source of a stationary CT system in accordance with another embodiment of the present invention.

Referring now to FIG. 8, a method of activating emitter elements of an x-ray source of a stationary CT system in accordance with another embodiment of the present invention is shown. Although the following steps are described with respect to the embodiments of FIGS. 5A and 6A, they can be easily modified with respect to other embodiments of the present invention.

In step 200, the counter 29 is initialized and set to have a zero value. In step 202, an emitter element, such as one of the emitter elements 81 corresponding to the value of the counter 29 is activated. The controller 28 generates activation signals that are received by the emitter element via the associated emitter element activation lines and emitter element connections, such as lines 90 and 114 and connections 92 and 116. In step 202A, a first series of emitter elements receives a first activation signal, such as elements along column A. In step 202B, a second series of emitter elements receives a second activation signal, such as elements along row W. When a series of emitter array blocks is utilized a block having the emitter element of concern may be addressed. In step 202C, when a three-dimensional scheme is utilized a third series of emitter elements, such as elements along line 7, may receive a third activation signal.

In step 204, electrons are emitted from the activated emitter element. In step 206, the value of the counter 29 is altered. The counter 29 may be incremented, as shown in FIG. 8, or may be simply altered such that a subsequently activated emitter element is different from a current emitter element. The controller 28 upon completion of step 206 returns to step 202.

The present invention provides multiple emitter element array configurations for an x-ray source that may be utilized within a SCT system. The present invention minimizes the number of feedthroughs necessary for operation of emitter elements within the SCT system. In so doing, the present invention decreases complexity and increases operation life and reliability of an x-ray source including short-term and long-term stability of the x-ray source. Also, fewer feedthroughs minimizes vacuum leaks of the x-ray source. The present invention also increases the flexibility in choice of emitter elements that may be utilized for a given application.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

The invention claimed is:

1. An x-ray source comprising:
   a vacuum housing;
   at least one emitter array generating at least one electron beam and having a plurality of emitter elements disposed within said vacuum housing, each of said emitter elements in said plurality of emitter elements having at least three activation connections;
   a source further comprising a plurality of AND gates coupled between said plurality of emitter elements and said plurality of activation connections, said plurality of AND gates activating said plurality of emitter elements; and
   a target disposed within said vacuum housing, receiving said at least one electron beam, and generating x-rays.

2. A source as in claim 1 wherein said vacuum housing is stationary.

3. A source as in claim 1 wherein at least one emitter element of said plurality of emitter elements is activated upon receiving an activation signal from each activation connection of said plurality of activation connections associated with said at least one emitter element.

4. A source as in claim 1 wherein said at least one emitter array are configured in a linear pattern.

5. A source as in claim 1 wherein said plurality of emitter elements are configured in a linear pattern.

6. A source as in claim 1 comprising at least one emitter array block, said at least one emitter array disposed within said at least one emitter array block.

7. A source as in claim 6 wherein said at least one emitter array block comprises at least one address line.

8. A source as in claim 6 wherein at least one emitter element of said plurality of emitter elements is activated upon addressing of said at least one block and receiving an activation signal from each activation connection of said plurality of activation connections associated with said at least one emitter element.

9. A source as in claim 6 wherein said at least one emitter array block comprises a plurality of emitter array blocks coupled in series.

10. A source as in claim 6 wherein said at least one emitter array block comprises:
    a first emitter array block having a first emitter array; and
    a second emitter array block having a second emitter array;
    wherein at least one emitter element connection in said first emitter array block is shared with at least one emitter element connection in said second emitter array block.

11. A source as in claim 1 wherein said plurality of emitter elements have a plurality of focusing control connections.

12. A source as in claim 1 wherein said plurality of emitter elements have a two-dimensional activation scheme and a one-dimensional physical configuration.

13. A source as in claim 1 wherein said plurality of emitter elements have a three-dimensional activation scheme and a one-dimensional physical configuration.

14. A source as in claim 1 wherein said plurality of emitter elements are activated sequentially.

15. A source as in claim 1 wherein said plurality of emitter elements are activated non-sequentially.

16. A stationary computed tomography source comprising:
    at least one vacuum housing;
    an elongated cathode emitter array generating a plurality of electron beams and having a plurality of emitter elements disposed within said at least one vacuum housing;
    at least one emitter array block, said elongated cathode emitter array disposed within said at least one emitter array block;
    a source further comprising a plurality of AND gates coupled between said plurality of emitter elements and said plurality of activation connections, said plurality of AND gates activating said plurality of emitter elements;
    each of said emitter elements in said plurality of emitter elements having a plurality of activation connections; and
    an elongated anode disposed within said at least one vacuum housing and spaced apart from said plurality of emitter elements.

17. A source as in claim 16 wherein at least one emitter element of said plurality of emitter elements is activated upon receiving an activation signal from each activation connection of said plurality of activation connections associated with said at least one emitter element.

18. A stationary computed tomography system comprising:
- a stationary gantry comprising;
- a plurality of x-ray sources surrounding a patient volume and generating at least one electron beam comprising:
- a vacuum housing;
- a plurality of emitter elements disposed within said vacuum housing; and
- each of said emitter elements in said plurality of emitter elements having a plurality of activation connections;
- a source further comprising a plurality of AND gates coupled between said plurality of emitter elements and said plurality of activation connections, said plurality of AND gates activating said plurality of emitter elements; and
- at least one detector receiving at least one x-ray beam generated in response to said at least one electron beam.

19. A system as in claim 18 wherein at least one emitter element of said plurality of emitter elements is activated upon receiving an activation signal from each activation connection of said plurality of activation connections associated with said at least one emitter element.

20. A system as in claim 18 further comprising at least emitter array block, said at least one emitter array disposed within said at least one emitter array block.

21. A system as in claim 18 wherein said at least one detector comprises a plurality of detectors opposing said plurality of x-ray sources about said patient volume and receiving said at least one x-ray beam.

22. A system as in claim 18 wherein said x-ray sources are semi-circular in shape.

23. A system as in claim 18 wherein said x-ray sources are stationary.

24. A method of activating emitter elements of a stationary x-ray source of a stationary CT system comprises:
- activating a first emitter element of an emitter array block corresponding to the value of a counter comprising:
- receiving a first activation signal by a first series of emitter elements of the stationary x-ray source, said first series of emitter elements activated by an AND gate coupled between said first series of emitter elements and a first activation connection; and
- receiving a second activation signal by a second series of emitter elements of the stationary x-ray source, said second series of emitter elements activated by an AND gate coupled between said second series of emitter element and a first activation connection; and
- emitting electrons from said first emitter element in response to said first activation signal and said second activation signal.

25. A method as in claim 24 further comprising:
incrementing said counter; and
sequentially activating a second emitter element adjacent said first emitter element.

26. A method as in claim 24 further comprising:
incrementing said counter; and
non-sequentially activating a second emitter element adjacent said first emitter element.

27. An x-ray source comprising:
a vacuum housing;
at least one emitter array generating at least one electron beam and having a plurality of emitter elements disposed within said vacuum housing;
each of said emitter elements in said plurality of emitter elements having a plurality of activation connections;
a source further comprising a plurality of AND gates coupled between said plurality of emitter elements and said plurality of activation connections, said plurality of AND gates activating said plurality of emitter elements;
at least one emitter array block, said at least one emitter array disposed within said at least one emitter array block; and
a target disposed within said vacuum housing, receiving said at least one electron beam, and generating x-rays.

* * * * *